United States Patent
Ishii et al.

(10) Patent No.: US 6,500,415 B2
(45) Date of Patent: Dec. 31, 2002

(54) COSMETIC COMPOSITION

(75) Inventors: Nobuaki Ishii, Kanagawa (JP); Junko Futami, Kanagawa (JP); Kouichi Wada, Kanagawa (JP); Michihiro Takama, Kanagawa (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 09/873,398

(22) Filed: Jun. 5, 2001

(65) Prior Publication Data

US 2002/0041853 A1 Apr. 11, 2002

Related U.S. Application Data

(60) Provisional application No. 60/272,779, filed on Mar. 5, 2001.

(30) Foreign Application Priority Data

Jun. 5, 2000 (JP) ......................................... 2000-167091

(51) Int. Cl.[7] ........................ A61K 31/74; A61K 7/42; A61K 7/44; A61K 7/06; A61K 7/00
(52) U.S. Cl. ........................ 424/78.03; 424/59; 424/60; 424/70.1; 424/401; 514/972
(58) Field of Search .................. 424/78.03, 5.9, 424/4.01, 70.1, 59, 60, 405; 514/972

(56) References Cited

U.S. PATENT DOCUMENTS

| | | |
|---|---|---|
| 5,145,719 A | 9/1992 | Towata et al. |
| 5,582,818 A * | 12/1996 | Nakanishi et al. ............. 424/59 |
| 5,587,148 A | 12/1996 | Mitchell et al. |
| 5,616,331 A | 4/1997 | Allard et al. |
| 5,695,747 A | 12/1997 | Forestier et al. |

FOREIGN PATENT DOCUMENTS

| | | | |
|---|---|---|---|
| EP | 559319 A2 | 9/1993 | |
| JP | 05-286721 | 11/1993 | |
| JP | 9-151110 | 6/1997 | ............ A61K/7/00 |
| JP | 11-217219 | 8/1999 | |
| JP | 11-256133 | 9/1999 | |
| JP | 11-302015 | 11/1999 | |
| WO | 94/15580 | 7/1994 | ............ A62K/7/42 |

OTHER PUBLICATIONS

International Search Report.

* cited by examiner

Primary Examiner—Thurman K. Page
Assistant Examiner—Blessing Fubara
(74) Attorney, Agent, or Firm—Sughrue Mion, PLLC

(57) ABSTRACT

A cosmetic composition comprising titanium oxide coated with one or both of silica and alumina or zinc oxide coated with one or both of silica and alumina, and a thickening polymer having a carboxyl group in the side chain, preferably a carboxyvinyl polymer, wherein when 10% by mass of silica- and/or alumina-coated titanium oxide or silica- and/or alumina-coated zinc oxide is dispersed in an aqueous solution containing 0.133% by mass of a carboxyvinyl polymer, the viscosity after the passing of 100 hours is 50% or more of the initial viscosity. A cosmetic composition comprising titanium oxide coated with one or both silica and alumina or zinc oxide coated with one or both of silica and alumina, and a thickening polymer having a carboxyl group in the side chain of the invention, can maintain emulsion stability by thickening of polymer for a long period of time and can be widely and suitably used for ultraviolet shielding cosmetic materials or the like having preparation form stability.

16 Claims, 1 Drawing Sheet

Light Transmittance of Titanium Oxide

US 6,500,415 B2

COSMETIC COMPOSITION

CROSS REFERENCE TO THE RELATED APPLICATIONS

This is an application based on the prescription of 35 U.S.C. Section 111(a) with claiming the benefit of filing date of U.S. Provisional applications Serial No. 60/272,779 filed Mar. 5, 2001 under the provision of 35 U.S.C. 111(b), pursuant to 35 U.S.C. Section 119(e)(1).

TECHNICAL FIELD

The present invention relates to a cosmetic composition, particularly a cosmetic composition having an ultraviolet shielding ability. More specifically, the present invention relates to a titanium oxide- or zinc oxide-containing cosmetic composition capable of maintaining the emulsion stability for a long period of time by virtue of thickening of a polymer having a carboxyl group in the side chain.

BACKGROUND ART

In cosmetic compositions having an ultraviolet shielding ability, an organic compound-based ultraviolet absorber or an inorganic compound-based ultraviolet shielding agent is blended.

The organic compound-based ultraviolet absorber has a problem of instability due to its decomposition property and therefore, an inorganic compound-based ultraviolet shielding agent is recently used in many cases. In particular, titanium oxide or zinc oxide is generally used.

The preparation form of the cosmetic composition having an ultraviolet shielding ability includes various shapes such as solubilized form, emulsion form (W/O type, O/W type, W/O/W), powder form and gel form. In the case of an O/W form or gel form, a thickening polymer having a carboxyl group in the side chain is preferably used as a thickener so as to increase stability of the preparation form.

Specific examples of the thickening polymer having a carboxyl group in the side chain include carboxyvinyl polymer, carboxymethyl cellulose, carboxymethyl starch, poly(sodium acrylate), alginic acid propylene glycol ester and alginic acid salt. Among these, carboxyvinyl polymer is used widely.

The carboxyvinyl polymer is characterized and advantageous in that high thickening stability can be obtained with a low concentration, that reproducibility which cannot be realized by natural polymers can be attained, that the temperature stability and microorganism resistance are high, that the pH and viscosity which can be used have a wide range, and that good use property is provided at the application to skin. Therefore, the carboxyvinyl polymer is being widely used in cosmetic materials. For example, JP-A-08-505624 (WO94/15580) discloses an oil-in-water emulsion composition comprising a fine pigment particle having the surface treated to be hydrophobic, and a carboxylic acid polymer thickener. JP-A-09-151110 discloses alkyl (meth) acrylate polymer as a thickener for a liquid cosmetic containing an inorganic powder such as titanium oxide.

In the case where the carboxyvinyl polymer is used in combination with titanium oxide or zinc oxide in an ultraviolet shielding cosmetic composition, the titanium oxide or zinc oxide used in combination for enhancing the ultraviolet shielding ability is likely formed into microfine particles and the resulting increase in the surface activity of titanium oxide or zinc oxide (catalytic action) causes deterioration of carboxyvinyl polymer. The surface activity can be suppressed to a certain extent by surface treatment with silica, alumina or the like, however, photocatalytic deterioration of carboxyvinyl polymer cannot be satisfactorily suppressed by conventional surface treatments. Accordingly, reduction of viscosity takes place in the gel-form preparation and separation or creaming in the emulsion-form preparation.

The carboxyvinyl polymer deteriorates in the preparation form stability due to the effect of metal ion, because the hydration degree of polymer is reduced by the reaction between metal ion and carboxyl group and therefore, the viscosity decreases. In conventional production of surface-treated titanium oxide or zinc oxide, the surface treatment uses precipitation of inorganic metal oxide from sodium silicate or sodium aluminate and since sodium ion remains, polyvalent ion such as calcium, magnesium and iron is contained as impurities in many cases.

Furthermore, conventional surface-treated zinc oxide is insufficient in the film formation and therefore, zinc ion is eluted accompanying the dissolution of zinc oxide. As a result, when conventional surface-treated titanium oxide or zinc oxide is used in combination with carboxyvinyl polymer, the viscosity decreases along the elution of ion and the preparation form stability disadvantageously deteriorates.

DISCLOSURE OF THE INVENTION

The object of the present invention is to provide an ultraviolet shielding cosmetic composition containing titanium oxide or zinc oxide, which can maintain the preparation (emulsion or gel) form stability for a long period of time by the thickening of carboxyvinyl polymer.

As a result of extensive investigations to attain the above-described object, the present inventors have found that a cosmetic composition having desired properties can be obtained when silica-coated titanium oxide or zinc oxide coated with a certain dense silica film is blended in combination with a polymer having a carboxyl group in the side chain. The present invention has been accomplished based on this finding.

More specifically, the present invention relates to the following cosmetic composition, silica-coated titanium oxide and/or silica-coated zinc oxide used for the cosmetic composition, and method for producing the same.

[1] A cosmetic composition comprising titanium oxide coated with one or both of silica and alumina or zinc oxide coated with one or both of silica and alumina, and a thickening polymer having a carboxyl group in the side chain.

[2] The cosmetic composition as described in [1] above, wherein the thickening polymer having a carboxyl group in the side chain is at least one polymer selected from a group consisting of carboxyvinyl polymer, carboxymethyl cellulose, carboxymethyl starch, poly(sodium acrylate), alginic acid propylene glycol ester and alginic acid salt.

[3] The cosmetic composition as described in [2] above, wherein the thickening polymer having a carboxyl group in the side chain is carboxyvinyl polymer.

[4] The cosmetic composition as described in [3] above, wherein when titanium oxide coated with one or both of silica and alumina or zinc oxide coated with one or both of silica and alumina is dispersed by 10% by mass in an aqueous solution containing 0.133% by mass of a carboxyvinyl polymer, the viscosity after the passing of 100 hours is 50% or more of the initial viscosity.

[5] The cosmetic composition as described in [4] above, wherein when titanium oxide coated with one or both of silica and alumina is dispersed by 10* by mass in an aqueous solution containing 0.133% by mass of a carboxyvinyl polymer, the viscosity after the passing of 100 hours is 70% or more of the initial viscosity.

[6] The cosmetic composition as described in [4] above, wherein when zinc oxide coated with one or both of silica and alumina is dispersed by 10% by mass in an aqueous solution containing 0.133% by mass of a carboxyvinyl polymer, the viscosity after the passing of 100 hours is 60% or more of the initial viscosity.

[7] The cosmetic composition as described in [1] above, which comprises silica-coated titanium oxide or silica-coated zinc oxide coated with a dense silica film having a film thickness of 0.1 to 100 nm and a refractive index of 1.435 or more.

[8] The cosmetic composition as described in [11] above, wherein the photocatalytic activity of the silica-coated titanium oxide or silica-coated zinc oxide determined by the tetralin auto-oxidation method is 60 Pa/min or less.

[9] The cosmetic composition as described in [1] above, wherein the silica-coated titanium oxide or silica-coated zinc oxide has a primary particle size of 5 to 200 nm.

[10] The cosmetic composition as described in [1] above, wherein the ratio I of absorption peak intensity at 1,150 to 1,250 $cm^{-1}$ to absorption peak intensity at 1,000 to 1,100 $cm^{-1}$ on the infrared absorption spectrum ($I=I_1/I_2$, wherein $I_1$, is absorption peak intensity at 1,150 to 1,250 $cm^{-1}$ and $I_2$ is absorption peak intensity at 1,000 to 1,100 $cm^{-1}$) is 0.2 or more.

[11] The cosmetic composition as described in [1] above, wherein the dye discoloration rate ($\Delta ABS_{490}$/hr) of the silica-coated titanium oxide or silica-coated zinc oxide measured by the Sunset Yellow method is 0.1 or less.

[12] The cosmetic composition as described in [1] above, wherein the organic ultraviolet absorber decomposition rate ($\Delta ABS_{340}$/hr) of the silica-coated titanium oxide or silica-coated zinc oxide measured by the Parsol method is 0.01 or less.

[13] The cosmetic composition as described in [1] above, wherein silica-coated titanium oxide or silica-coated zinc oxide is blended in an amount of 0.1 to 50% by mass based on the entire amount of cosmetic composition.

[14] A silica-coated titanium oxide or silica-coated zinc oxide used for the cosmetic composition described in [1] above, which is obtained by coating titanium oxide or zinc oxide with a silica film-forming composition containing (1) a silicic acid having neither an organic group nor a halogen, or a precursor capable of producing the silicic acid, (2) water, (3) an alkali and (4) an organic solvent.

[15] The silica-coated titanium oxide or silica-coated zinc oxide as described in [14] above, which is obtained by contacting titanium oxide or zinc oxide with the silica film-forming composition having a water/organic solvent ratio (volume) of 0.1 to 10 and a silicic acid concentration of 0.0001 to 5 mol/liter to selectively deposit silica on the surface of titanium oxide or zinc oxide.

[16] A method for producing a silica-coated titanium oxide or silica-coated zinc oxide used for the cosmetic composition described in any one of [1] to [13] above, comprising coating titanium oxide or zinc oxide with a silica film-forming composition containing (1) a silicic acid having neither an organic group nor a halogen or a precursor capable of producing the silicic acid, (2) water, (3) an alkali and (4) an organic solvent.

[17] The method for producing the silica-coated titanium oxide or silica-coated zinc oxide as described in [16] above, comprising contacting titanium oxide or zinc oxide with the silica film-forming composition having a water/organic solvent ratio (volume) of 0.1 to 10 and a silicic acid concentration of 0.0001 to 5 mol/liter to selectively deposit silica on the surface of titanium oxide or zinc oxide.

MODE FOR CARRYING OUT THE INVENTION

The mode for carrying out the invention is described in detail below, however, the present invention is not limited thereto.

The present invention is described by taking silica-coated titanium oxide or silica-coated zinc oxide as an example out of titanium oxide and zinc oxide coated with silica, alumina or both silica and alumina which can be used in the present invention.

In the cosmetic composition of the present invention, a silica-coated titanium oxide or a silica-coated zinc oxide may be suitably used, which is obtained by a method of contacting titanium oxide powder or zinc oxide powder with a silica film-forming composition comprising silicic acid, water, an alkali and an organic solvent and having a water/organic solvent ratio by volume of 0.1 to 10 and a silicon concentration of 0.0001 to 5 mol/liter to selectively deposit dense silica on the surface of titanium oxide powder or zinc oxide powder.

In the silica-coated titanium oxide or silica-coated zinc oxide coated with a dense silica film, which can be more suitably used in the cosmetic composition of the present invention, the ratio I of absorption peak intensity at 1.150 to 1,250 $cm^{-1}$ to absorption peak intensity at 1,000 to 1,100 $cm^{-1}$ on the infrared absorption spectrum ($I=I_1/I_2$, wherein $I_1$, is absorption peak intensity at 1,150 to 1,250 $cm^{-1}$ and $I_2$ is absorption peak intensity at 1,000 to 1,100 $cm^{-1}$) is 0.2 or more and the refractive index is 1.435 or more.

The silicic acid for use in the silica film-forming composition indicates orthosilicic acid or a polymer thereof having no organic group and halogen such as metasilicic acid, mesosilicic acid, mesotrisilicic acid and mesotetrasilicic acid, which are described, for example, in the paragraph "Silicic Acid" of *Encyclopaedia Chimica*, 7th imp., Kyoritsu Shuppan (Mar. 15, 1969).

The composition containing silicic acid can be obtained by adding water, an alkali and an organic solvent to tetraalkoxysilane ($Si(OR)_4$, wherein R is a hydrocarbon group (specific examples thereof include tetramethoxysilane, tetraethoxysilane, tetra-n-propoxysilane, tetraisopropoxy silane and tetra-n-butoxy silane)), stirring the mixture and thereby allowing a hydrolysis reaction to proceed. This method is practical and preferred because of easiness in handling or operation. Among those materials, tetraethoxysilane is preferred.

The composition containing silicic acid can also be obtained by a method of hydrolyzing silane tetrahalogenide by adding thereto water, an alkali and an organic solvent, a method of adding an alkali and an organic solvent to water glass, or a method of treating water glass with a cationic exchange resin and adding thereto an alkali and an organic solvent. Tetraalkoxysilane, silane tetrahalogenide or water glass used as the starting material of silicic acid is not particularly limited and one used in industry or widely known as a reagent may be used, however, a higher purity material is suitable. The silica film-forming composition for use in the present invention may contain an unreacted material of the above-described starting material for silicic acid.

The amount of silicic acid is not particularly limited but is preferably from 0.0001 to 5.0 mol/liter, in terms of the silicon concentration. If the silicon concentration is less than 0.0001 mol/liter, the silica film is formed at a very low rate and this is not practical, whereas if it exceeds 5 mol/liter, the coating is not formed and silica particles may be produced in the composition.

The silicon concentration may be calculated from the amount of, for example, tetraalkoxysilane added but can also be measured by atomic absorption spectrochemical analysis of the composition. The measurement may be performed using a spectrum at a wavelength of 251.6 nm for the analytical line and acetylene/nitrous oxide for the frame.

The water used in the silica film-forming composition is not particularly limited but is preferably water from which particles are removed by filtration or the like. If the water contains particles, the particles maybe disadvantageously mixed into the product as an impurity.

The water is preferably used in an amount of 0.1 to 10 in terms of the water/organic solvent ratio by volume. If the water/organic solvent ratio by volume exceeds or is less than this range, the coating may not be formed or the film formation rate may extremely decreases. The water/organic solvent ratio by volume is preferably from 0.1 to 5 and more preferably from 0.1 to 0.5. Insofar as the water/organic solvent ratio by volume is from 0.1 to 5, the kind of alkali used is not limited. In the case where the water/organic solvent ratio by volume is 5 or more, the coating is preferably formed using an alkali metal-free alkali such as ammonia, ammonium hydrogencarbonate and ammonium carbonate.

The alkali used in the silica film-forming composition for use in the present invention is not particularly limited but examples of the alkali which can be used include inorganic alkalis such as ammonia, sodium hydroxide and potassium hydroxide; inorganic alkali salts such as ammonium carbonate, ammonium hydrogencarbonate, sodium carbonate and sodium hydrogencarbonate; organic alkalis such as monomethylamine, dimethylamine, trimethylamine, monoethylamine, diethylamine, triethylamine, pyridine, aniline, choline, tetramethylammonium hydroxide and guanidine; and alkaline salts of organic acid, such as ammonium formate, ammonium acetate, monomethylamine formate, dimethylamine acetate, pyridine lactate, guanidinoacetic acid and aniline acetate.

Among these, in view of control of the reaction rate, ammonia, ammonium carbonate, ammonium hydrogencarbonate, ammonium formate, ammonium acetate, sodium carbonate and sodium hydrogencarbonate are preferred. The above-described alkalis for use in the silica film-forming composition may be used individually or in combination of two or more thereof.

The purity of alkali for use in the present invention is not particularly limited and an alkali used in industry or widely known as a reagent may be used, but a higher purity alkali is preferred.

The silica film-forming rate may be effectively increased by elevating the temperature at the film formation. In this case, an alkali and an organic solvent which are not easily volatilized or decomposed at the film formation temperature are preferably used.

With respect to the amount of alkali used for film formation in the present invention, for example, in the case of sodium carbonate, the coating may be formed by adding the alkali in a trace amount of about 0.002 mol/liter but the alkali may also be added in a large amount of about 1 mol/liter. However, if a solid alkali is added in excess of solubility, the alkali is disadvantageously mixed into the metal oxide powder as an impurity.

By using an alkali not containing an alkali metal as a main component, silica-coated metal oxide powder having a small alkali metal content can be prepared. In this case, ammonia, ammonium carbonate and ammonium hydrogencarbonate are preferred in view of the film formation rate and easiness in the removal of residual matter.

In the present invention, the organic solvent for use in the silica film-forming composition is preferably an organic solvent which provides the composition as a uniform solution. Examples thereof include alcohols such as methanol, ethanol, propanol and pentanol; ether.acetals such as tetrahydrofuran and 1,4-dioxane; aldehydes such as acetaldehyde; ketones such as acetone, diacetone alcohol and methyl ethyl ketone; and polyhydric alcohol derivatives such as ethylene glycol, propylene glycol and diethylene glycol. Among these, in view of control of the reaction rate, alcohols are preferred and ethanol is more preferred. These organic solvents may be used either individually or in combination of two or more thereof.

The purity of the organic solvent for use in the silica film-forming composition is not particularly limited and an organic solvent used in industry or commonly used over a wide range as a reagent may be used, but a higher purity organic solvent is preferred.

In preparing the silica film-forming composition, a general method for preparing a solution may be applied. For example, a method of adding an alkali and water each in a predetermined amount to an organic solvent, followed by stirring, and then adding tetraethoxysilane, followed by stirring may be used. Whichever added earlier in the mixing, a coating can be formed. In mixing water and tetraethoxysilane, both are preferably diluted with an organic solvent in view of control of the reaction.

The thus-prepared silica film-forming composition is a stable composition and causes substantially no deposition or precipitation before the composition is brought into contact with metal oxide powder. When the metal oxide powder is contacted with the composition, silica starts to selectively deposit on the surface of the metal oxide powder.

The production method of titanium oxide as a starting material of the silica-coated titanium oxide is not particularly limited and any method may be used. A titanium oxide produced by any production method such as high-temperature vapor phase oxidation of $TiCl_4$, vapor phase hydrolysis of $TiCl_4$, sulfuric acid process and chlorine process, may be used. With respect to the crystal form of titanium oxide, any of amorphous, rutile, anatase and brookite may be used and a mixture thereof may also be used. In view of control of the secondary particle size, the titanium oxide is preferably reduced in impurities as much as possible, more preferably reduced in the coagulation.

The production method of zinc oxide as a starting material of the silica-coated zinc oxide is not particularly limited and any method may be used. A zinc oxide produced by evaporation oxidation of electrolytic zinc metal, or produced by calcining zinc hydroxide, zinc carbonate, zinc sulfide, zinc oxalate or the like which are obtained by neutralizing an aqueous solution of water-soluble salt such as zinc sulfate and zinc chloride, or a mixture of the above-mentioned zinc oxide may be used. However, in view of control of the secondary particle size, the zinc oxide is preferably reduced in impurities as much as possible, more preferably reduced in the coagulation.

In the present invention, the silica film can be formed by immersing titanium oxide or zinc oxide in the silica film-forming composition and keeping it at a predetermined temperature to selectively deposit silica on the surface of titanium oxide or zinc oxide. Also, a method of previously preparing the film-forming composition and charging titanium oxide or zinc oxide in the composition, a method of previously suspending titanium oxide or zinc oxide in a solvent, adding other raw material components to prepare a film-forming composition and forming the silica film, or the like may be used. In other words, the order of charging raw materials of the film-forming composition and titanium oxide or zinc oxide is not particularly limited and whichever charged earlier, a silica film can be formed.

Among these methods, a method of preparing a suspension containing titanium oxide or zinc oxide, water, an organic solvent and an alkali, and adding thereto dropwise tetraalkoxysilane diluted with an organic solvent at a constant rate is preferred, because a denser silica film can be formed and a continuous process useful in industry can be established.

The silica film grows by the deposition on the surface of metal oxide and therefore, as the film formation time is longer, the coating can have a larger thickness. Of course, when the majority of silicic acid in the film-forming composition is consumed by the formation of coating, the film formation rate decreases, however, by sequentially adding silicic acid in an amount corresponding to the consumed portion, the silica film can be continuously formed at a practical film formation rate. In particular, when the silica film is formed by holding titanium oxide in the film-forming composition having added thereto a silicic acid corresponding to the desired thickness of silica film for a predetermined time and thereby the silicic acid is consumed, a silicic acid corresponding to the consumed portion may be further added after the silica-coated titanium oxide or silica-coated zinc oxide is taken out from the system, whereby the composition can be continuously used in the film formation on next titanium oxide or zinc oxide and a continuous process having high profitability and good productivity can be established.

In the case of a method of preparing a suspension containing titanium oxide or zinc oxide, water, an organic solvent and an alkali and adding thereto dropwise tetraalkoxysilane diluted with an organic solvent at a constant rate, a solution obtained by diluting tetraalkoxysilane corresponding to the desired thickness of silica film with an organic solvent is added dropwise at a constant rate agreeing with the hydrolysis rate, whereby the tetraalkoxysilane is completely consumed, a dense silica film having a desired thickness can be formed and when the produced silica-coated titanium oxide is taken out from the system, a high-purity product free of residual unreacted tetraalkoxysilane can be obtained. Of course, the solvent after the silica-coated titanium oxide or silica-coated zinc oxide is taken out can be recycled in the next film formation and thereby, a process favored with high profitability and high productivity can be established.

The temperature at the formation of silica film is not particularly limited but is preferably from 10 to 100° C., more preferably from 20 to 50° C. As the temperature is higher, the film formation rate is more increased, however, if the temperature is excessively high, the solution composition may not be maintained constant due to volatilization of components in the composition, whereas if the temperature is too low, the film formation proceeds at a low rate and this is not practical.

The pH at the film formation may be sufficient if it is in the alkali region. However, in the case of forming the silica film on a metal oxide having a solubility which increases depending on the pH, the pH of the film-forming composition is preferably controlled.

After the film formation, the silica-coated titanium oxide or silica-coated zinc oxide can be isolated by solid-liquid separation. The isolation may be performed by a general separation method such as filtration, centrifugal sedimentation and centrifugal separation.

By performing drying after the solid-liquid separation, silica-coated titanium oxide or zinc oxide reduced in the water content can be obtained. In the drying, a general drying method may be used, such as natural drying, hot air drying, vacuum drying and spray drying. In the case where coagulation of particles occurs by the drying, the aggregate may be ground.

In the silica-coated titanium oxide or silica-coated zinc oxide of the present invention, the silica film has a very high shape-following capability and since primary particles of titanium oxide or zinc oxide as a substrate each is coated with a dense silica film having high covering power, the silica film is not broken by the grinding. The grinding method is not particularly limited and a jet mill, a high-speed rotary mill or the like may be used.

In the silica film obtained by the above-described method, the ratio I of absorption peak intensity at 1,150 to 1,250 $cm^{-1}$ to absorption peak intensity at 1,000 to 1,100 $cm^{-1}$ on the infrared absorption spectrum ($I=I_1/I_2$, wherein $I_2$ is absorption peak intensity at 1,150 to 1,250 $cm^{-1}$ and $I_2$ is absorption peak intensity at 1,000 to 1,100 $cm^{-1}$) is 0.2 or more and the refractive index is 1.435 or more. The silica coating, as having a chemical bond or a functional group of silica film formed while not performing calcination in a conventional sol-gel method, exhibits specific physical properties different in the hydrophilicity, lipophilicity or the like from silica film obtained through calcination. Nevertheless, this silica coating is dense and practical.

The term "dense" as used in the present specification means that the silica film formed has a high density and is uniform and free of pin holes or cracks. The term "practical" as used means that the bonding between silica and the substrate metal oxide (—Si—O—M— bonding, wherein M is Ti or Zn) is strong enough not to cause stripping or the like of the coating and the physical properties of silica-coated titanium oxide or silica-coated zinc oxide are not readily changed.

Furthermore, this silica film has good compatibility with the complicated shape of substrate titanium oxide or zinc oxide and even if the thickness is as small as about 0.5 nm, the film exhibits good covering power and high capability of masking the photocatalytic activity. Furthermore, since the silica film can be very reduced in the alkali metal content, the silica film is not dissolved even in an atmosphere of high temperature and high humidity and the physical properties of the silica-coated titanium oxide are not changed.

The silica-coated titanium oxide or silica-coated zinc oxide for use in the cosmetic composition of the present invention has a silica film thickness of 0.1 to 100 nm, preferably from 0.5 to 25 nm. If the thickness of silica film is less than 0.1 nm, a sufficiently high effect of masking the photocatalytic activity cannot be obtained and the cosmetic composition obtained cannot have preparation form stability in some cases, whereas if it exceeds 100 nm, a cosmetic composition having sufficiently high ultraviolet shielding ability may not be obtained and therefore, this is not preferred.

The silica-coated titanium oxide or silica-coated zinc oxide for use in the present invention has a primary particle size of 5 to 200 nm, preferably from 5 to 120 nm. If the primary particle size departs from this range, a cosmetic composition having a high ultraviolet shielding ability may not be obtained and therefore, this is not preferred.

The term "primary particle" as used in the present invention indicates a particle defined in Kiichiro Kubo et al., *Funtai (Powder)*, pp. 56–66 (1979).

The photocatalytic activity measured by the tetralin auto-oxidation method of the silica-coated titanium oxide or silica-coated zinc oxide for use in the present invention is 60 Pa/min or less, preferably 50 Pa/min or less. If the photocatalytic activity measured by the tetralin auto-oxidation method exceeds this range, a sufficiently high effect of masking the photocatalytic activity may not be obtained and the obtained cosmetic composition disadvantageously may fail in having preparation form stability.

The dye discoloration rate measured by the Sunset Yellow method (See below for further details) of the silica-coated titanium oxide or silica-coated zinc oxide for use in the present invention is preferably 0.1 or less, more preferably 0.05 or less. If it exceeds 0.1, the effect of masking the photocatalytic activity is not sufficiently high the obtained cosmetic composition may fail in having high preparation form stability.

The organic ultraviolet absorber decomposition rate measured by the Parsol method (See below for further details) of the silica-coated titanium oxide or silica-coated zinc oxide for use in the present invention is preferably 0.02 or less, more preferably 0.01 or less. If it exceeds 0.02, the effect of masking the photocatalytic activity is not sufficiently high and the obtained cosmetic composition may fail in having high preparation form stability.

The silica-coated titanium oxide or silica-coated zinc oxide for use in the present invention need not be particularly calcined but, of course, may be calcined before use.

The surface of the silica-coated titanium oxide or silica-coated zinc oxide for use in the present invention may be treated to be hydrophobic. Particularly, in the case of dispersing in oil at cosmetic formulation, those with the surface hydrophobitized are preferably used. In order to impart hydrophobicity, a method which comprises treating with one or more hydrophobicity-imparting materials selected from the group consisting of silicone oils, alkoxysilanes, silane coupling agents and higher fatty acid salts to coat the surface, may be applicable.

Examples of the hydrophobicity-imparting material include higher fatty acids such as wax, higher fatty acid glyceryl ester, higher fatty acid, higher fatty acid polyvalent metal salt and sulfonated aliphatic higher compound polyvalent metal salt; higher alcohol and the derivatives thereof; organic fluorine compounds such as per-fluorinated or partial-fluorinated higher fatty acid and per-fluorinated or partial-fluorinated higher alcohol; organic silicon compounds such as silicone oil dimethylpolysiloxane, methylhydrogenpolysiloxane, modified silicone oil), silane coupling agent, alkoxysilanes, chlorosilanes and silazanes. Among these, higher fatty acid polyvalent metal salt, silicone oil, silane coupling agent or alkoxysilanes is preferred. In view of practical effect, alkoxysilanes or silane coupling agent is more preferable. Surface treatment with alkoxysilanes can be carried out by a liquid phase method or a dry method. Preferred is a liquid phase method for the following reason. According to the method which comprises silica-coating by contacting the metal oxide fine particle with a silica film-forming composition, adding thereto hydrophobicity-imparting material without separating the fine particle, and if necessary, adding an alkali, water and a solvent, surface treatment of the silica-coated metal oxide with hydrophobicity-imparting material can be carried out continuously. Intermediate processes for separation and purification can be omitted in this method, therefore it is an industrially advantageous production method.

The coating amount of hydrophobicity-imparting material may be minimal amount or more for coating the surface of the silica-coated metal oxide particle completely with the hydrophobicity-imparting material. The upper limit of the addition amount of hydrophobicity-imparting material can not be generalized, but addition to excess is uneconomical because an amount of deposit other than the deposit on the surface of the silica-coated metal oxide particle increases. Generally, the amount of hydrophobicity-imparting material added is preferably from 0.5 to 30% by mass to the silica-coated metal oxide particle, and more preferably from 0.5 to 20% by mass. If the coating amount is less than 0.5% by mass, hydrophobicity is reduced, whereas if it exceeds 20% by mass, ultraviolet shielding ability may be reduced.

The polymer having a carboxyl group in the side chain is used for the cosmetic composition of the present invention. Examples of the polymer having a carboxyl group in the side chain include carboxyvinyl polymer, carboxymethyl cellulose, carboxymethyl starch, poly(sodium acrylate), alginic acid propylene glycol ester and alginic acid salt. Among these, carboxyvinyl polymer is preferred.

Mode for using the carboxyvinyl polymer is described below.

The carboxyvinyl polymer is mainly white fine powder obtained by forming an acrylic acid into a polymer by a solution polymerization and drying the polymer. This polymer is soluble in water. The solvent used for the polymerization may be benzene, ethyl acetate, a mixed solvent of ethyl acetate and cyclohexane, or the like. Since the solvent may remain and cause a problem in the safety, a mixed solvent of ethyl acetate and cyclohexane is preferably used in view of the product quality. The characteristic feature of carboxyvinyl polymer is attributed to the carboxyl group in the polymer. The polymer in the powder state is rigid and coiled due to no solvation. When the polymer is dispersed in water, the molecules are hydrated and the coiled state is loosened to a certain extent, whereby the viscosity increases.

When the polymer is further neutralized with an alkali, the carboxyl group is ionized to generate minus charge along the polymer skeleton and the resiliency thereof causes swelling, as a result, thickening abruptly occurs. By virtue of this thickening effect, the carboxyvinyl polymer is used in many cases for the purpose of stabilizing the preparation form of cosmetic composition, particularly an O/W emulsion such as cream and lotion, or a gel-like cosmetic material. The carboxyvinyl polymer is advantageous in that high thickening stability can be obtained with a low concentration, that reproducibility which cannot be realized by natural polymers can be attained, that the temperature stability and microorganism resistance are high, that the pH and viscosity which can be used have a wide range, and that good use property is provided at the application to skin. Therefore, the carboxy polymer is being more widely used in cosmetic materials as compared with other thickeners.

The viscosity behavior of carboxyvinyl polymer differs depending on the molecular weight, the degree of crosslinking, the molecular structure or the like, and the adaptability to cosmetic preparations also differs, however, the physical properties of the carboxyvinyl polymer which can be used in the cosmetic composition of the present invention are not particularly limited as long as these satisfy the Standards of Cosmetic Ingredients. Examples of the carboxyvinyl polymer which can be used in the cosmetic composition of the present invention include "CARBOPOL", a trade name, produced by BFGoodrich.

The cosmetic composition of the present invention is produced by a conventional method using the above-described silica-coated titanium oxide or silica-coated zinc oxide and the carboxyvinyl polymer together with conventional raw materials which can be used for a cosmetic composition.

The cosmetic composition of the present invention is, but not limited to, a cosmetic composition having a liquid form and specific examples thereof include cream, essence, lotion, skin lotion, milky lotion and jell.

The cosmetic composition of the present invention is composed of a powder portion and an oil portion. The material constituting the powder portion includes, in addition to the silica-coated titanium oxide or silica-coated zinc oxide, an extender pigment (e.g., mica, talc, kaolin, calcium carbonate, magnesium carbonate, silicic acid anhydride, aluminum oxide, barium sulfate), a white pigment (e.g., titanium dioxide, zinc oxide) and a color pigment (e.g., red oxide of iron, yellow oxide of iron, black oxide of iron, chromium oxide, ultramarine, iron blue, carbon black). These materials may be appropriately blended. In order to further improve the feeling on use, a spherical powder (e.g., nylon powder, polymethyl methacrylate powder) may also be used. Furthermore, similarly to the silica-coated titanium oxide or silica-coated zinc oxide, fine particulate cerium oxide or the like may be used for preventing ultraviolet rays, and this particle is also preferably coated with the dense silica film of the present invention.

Examples of the oil portion blended in the cosmetic composition of the present invention include liquid petrolatum, squalane, castor oil, glyceryl diisostearate, glyceryl triisostearate, glyceryl tri-2-ethylhexanoate, isopropyl myristate, dimethylpolysiloxane, methylphenylpolysiloxane, petrolatum, diisostearyl maleate and purified lanolin.

In the oil portion, an organic ultraviolet absorber may also be blended. The organic ultraviolet absorber means an organic compound having a function of absorbing an ultraviolet ray, consuming the energy for the generation of heat, oscillation, fluorescence, radical or the like, and thereby protecting skin. The ultraviolet absorber which can be used in the cosmetic composition of the present invention is not particularly limited but examples thereof include ultraviolet absorbers of benzophenone type, salicylic acid type, PABA type, cinnamic acid type, dibenzoylmethane type and urocanic acid type. For example, 2-hydroxy-4-methoxybenzophenone, 2-hydroxy-4-methoxybenzophenone-5-sulfonic acid, sodium 2-hydroxy-4-methoxybenzophenone-5-sulfonate, dihydroxydimethoxybenzophenone, sodium dihydroxydimethoxybenzophenone-sulfonate, tetrahydroxybenzo-phenone, p-aminobenzoic acid, ethyl p-aminobenzoate, glyceryl p-aminobenzoate, amyl p-dimethylaminobenzoate, octyl p-dimethylaminobenzoate, ethyl p-methoxycinnamate, isopropyl p-methoxycinnamate, octyl p-methoxycinnamate, 2-ethylhexyl p-methoxycinnamate, sodium p-methoxycinnamate, glyceryl bis(p-methoxycinnamate) mono(2-ethylhexanoate), octyl salicylate, phenyl salicylate, homomenthyl salicylate, dipropylene glycol salicylate, ethylene glycol salicylate, myristyl salicylate, methyl salicylate, urocanic acid, ethyl urocanate, 4-t-butyl-4'-methoxydibenzoylmethane, 2-(2'-hydroxy-5'-methylphenyl)benzotriazole, methyl anthranilate, or the like is used.

The amount of the ultraviolet absorber blended is from 0.1 to 10% by mass, however, an appropriate amount is preferably determined according to the ultraviolet ray-absorbing power of the absorber. The silica-coated titanium oxide or silica-coated zinc oxide for use in the present invention has a high effect of masking the photocatalytic activity and therefore, even when the metal oxide is used in combination with the organic ultraviolet absorber, the absorber can be prevented from decomposition, so that a cosmetic composition having high ultraviolet shielding ability can be provided and also, the carboxyvinyl polymer can be prevented from ultraviolet deterioration and more increased in the preparation form stability.

The cosmetic composition of the present invention may also contain an existing emulsifier in a general concentration. Examples of the emulsifier include those described in *Japanese Standards of Cosmetic Ingredients (JSCI), 2nd Edition. Annotation*, compiled by Nippon Koteisho Kyokai, issued by Yakuji Nippo, Ltd. (1984), *Specifications of Ingredient Other Than Those Listed in JSCI*, supervised by Examination Division, Pharmaceutical Affairs Bureau, Ministry of Health and Welfare, issued by Yakuji Nippo, Ltd. (1993), *Specifications of Ingredient Other Than Those Listed in JSCI. Supplement*, supervised by Examination Division, Pharmaceutical Affairs Bureau, Ministry of Health and Welfare, issued by Yakuji Nippo, Ltd. (1993), *The Comprehensive Licensing Standards of Cosmetics by Category*, supervised by Examination Division, Pharmaceutical Affairs Bureau, Ministry of Health and Welfare, issued by Yakuji Nippo, Ltd. (1993), and *Kesho-hin Genryo Jiten (Handbook of Cosmetic Ingredients)*, Nikko Chemicals (1991). All emulsifies described in these publications can be used. Furthermore, tocopheryl phosphates may also be used as the emulsifier.

In the cosmetic composition of the present invention, an existing antiinflammatory or antiphlogistic ingredient may be used in combination or may be mixed. The antiphlogistic ingredient which can be used in the present invention is not particularly limited, but examples thereof include aniline derivative-type antiphlogistic, salicylic acid derivative-type antiphlogistic, pyrazolone derivative-type antiphlogistic, indomethacin-type antiphlogistic, mefenamic acid-type antiphlogistic, antarthritic, spasmolytic, antitussive, expectorant, bronchodilator, respiratory function ameliorator, antihistamine agent, antiallergic agent and antiinflammatory enzymatic agent.

When an antioxidant as a substance having an oxidation-inhibiting activity is used in combination in the cosmetic composition of the present invention, the amount of free radicals generated by ultraviolet rays can be suppressed low, whereby the photocatalytic activity of silica-coated titanium oxide or silica-coated zinc oxide can be more reduced and therefore, a safe cosmetic composition having a remarkably excellent preparation stability and a low phototoxicity can be obtained.

The antioxidant having an effect of suppressing the photocatalytic activity for use in the cosmetic composition of the present invention is not particularly limited, but examples thereof include vitamin A, β-carotene, astaxanthin, vitamin B, vitamin C, magnesium L-ascorbic acid-2-phosphate, sodium L-ascorbic acid-2-phosphate, magnesium sodium L-ascorbic acid-2-phosphate, L-ascorbic acid-2-glucoside, L-ascorbic acid-2-phosphoric acid-5,6-benzylidene, natural vitamin E, dl-α-tocopherol, dl-α-tocopheryl acetate, sodium dl-α-tocopheryl phosphate, ubiquinone, derivatives of these vitamins, cysteine, glutathione, glutathioneperoxidase, SOD, catalase, citricacid, phosphoric acid, polyphenol, catechine, tea extract, kojic acid, nucleic acid, hydroquinone and arbutin. One or more selected from these antioxidants may be blended.

Other than the above-described ingredients, the cosmetic composition of the present invention may contain ingredients commonly blended in cosmetic compositions, such as fats and oils, waxes, hydrocarbons, fatty acids, alcohols, polyhydric alcohols, saccharides, esters, metal soap, water-soluble polymer compound, surfactant, antioxidant, microbicide antiseptic, vitamin, hormone and coloring material.

The amount of the silica-coated titanium oxide or silica-coated zinc oxide blended in the cosmetic composition of the present invention is from 0.1 to 50% by mass, preferably from 0.5 to 35% by mass, still more preferably from 1 to 20% by mass, based on the cosmetic composition.

The titanium oxide used for the purpose of shielding ultraviolet rays generally has a higher proportion of rutile form than anatase form. However, the silica-coated titanium oxide for use in the cosmetic composition of the present invention is greatly reduced in free radicals generated by ultraviolet rays and therefore, irrespective of the crystal form, a safe cosmetic composition favored with excellent preparation form stability and low phototoxicity can be obtained.

The cosmetic composition of the present invention not only has preparation form stability and ultraviolet shielding ability but also even when titanium oxide or zinc oxide is blended in a high concentration, ensures excellent feeling on use without causing any creaky feeling or poor extension. The cosmetic composition of the present invention has high transparency and does not cause pale finish on makeup as encountered in the case of containing a conventional titanium oxide or zinc oxide powder. Furthermore, photocatalytic activity of titanium oxide or zinc oxide is sufficiently masked and therefore, extremely high storage stability can be obtained without accelerating denaturation of other ingredients in the composition. An organic ultraviolet absorber can be contained and therefore, higher ultraviolet shielding effect and preparation form stability can be achieved. Still further, by containing an antioxidant having an oxidation-inhibiting activity, the generation of active oxygen or the like can be greatly reduced and the safety to the human body can be elevated.

In the present invention, the thickness and the refractive index of silica film can be measured by using a silica film formed on a silicon wafer immersed in a system undergoing the synthesis of silica-coated titanium oxide or silica-coated zinc oxide. On this silicon wafer, the same silica film as on the metal oxide is formed. The refractive index of silica film can be determined by an ellipsometer (LASSER ELLIPSOMETER ESM-1A, manufactured by ULVAC). The thickness can be determined using a step gauge.

The infrared absorption spectrum (FT-IR-8000 manufactured by Nippon Bunko) of silica film of the silica-coated titanium oxide or silica-coated zinc oxide can be determined by the KBr method. The primary particle size of silica-coated titanium oxide or silica-coated zinc oxide and the thickness of silica film thereof can be determined from an image by a transmission type electron microscope.

The photocatalytic activity, namely, the initial oxygen consumption rate of silica-coated metal titanium oxide or silica-coated zinc oxide of the present invention can be measured by the tetralin auto-oxidation method (see, Manabu Kiyono, *Sanka Titan-Bussei to Oyo Gijutsu* (*Titanium Oxide—Physical Properties and Applied Technique*), pp. 196–197, Gihodo (1991)). The measurement conditions are such that the temperature is 40° C., tetralin is 20 ml and titanium oxide is 0.02 g.

The photocatalytic activity of silica-coated titanium oxide or silica-coated zinc oxide for use in the present invention is further determined as a dye discoloration rate by the Sunset Yellow method or an organic ultraviolet absorber decomposition rate by the Parsol method, which are described in the present specification.

The light transmittance of silica-coated titanium oxide or silica-coated zinc oxide for use in the present invention is determined by the Cosmol method described in the present specification.

BEST MODE FOR CARRYING OUT THE INVENTION

Figure 1:
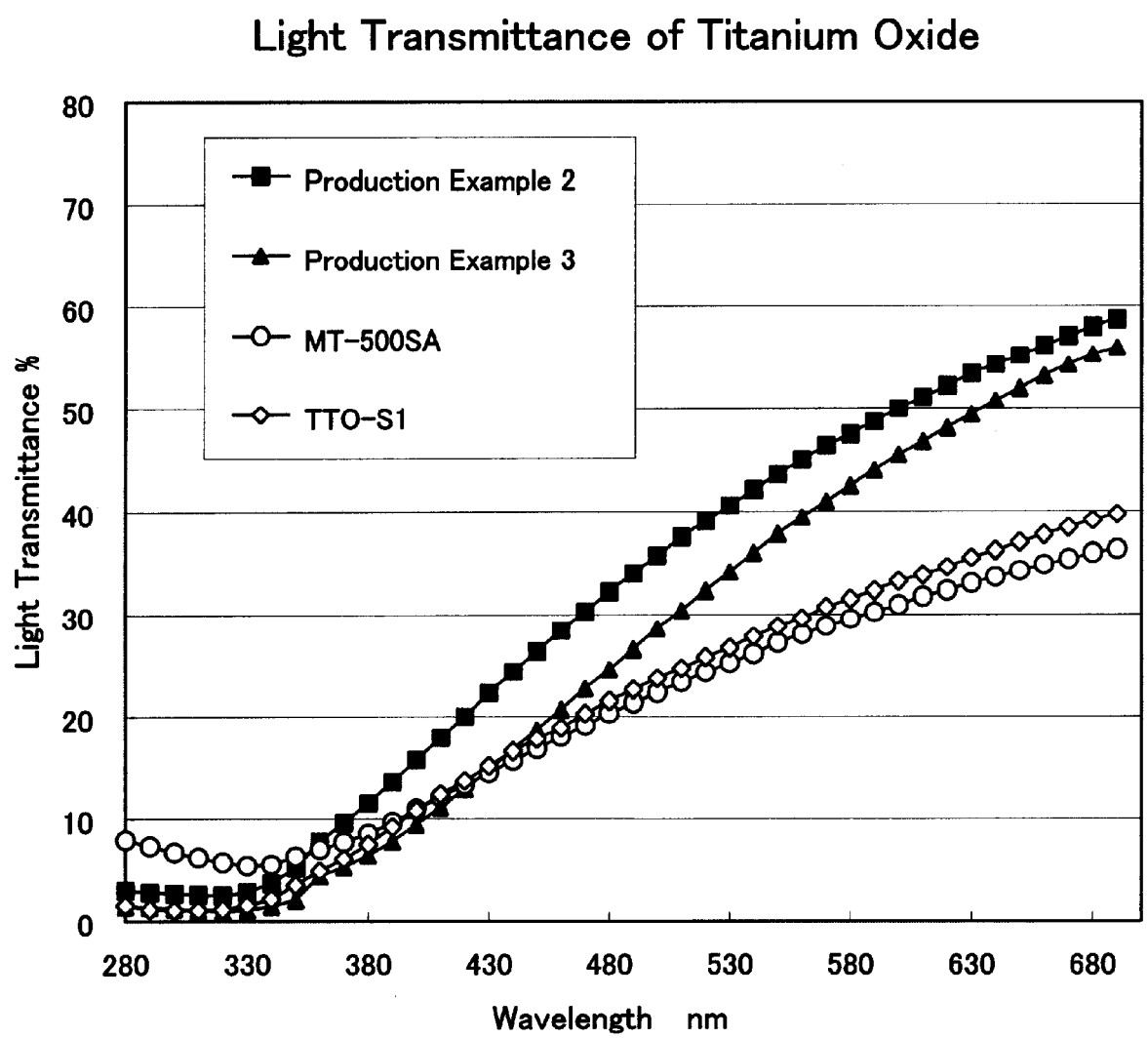
FIG. 1 is a diagram showing light transmittance of silica-coated titanium oxide produced by Production Example 2 and 3 according to the invention and two kinds of conventional surface-treated titanium oxide measured by the Cosmol method at a concentration of 1 mass % in a 0.1 mm quartz cell using a spectrophotometer.

The present invention is described in greater detail below by referring to the Production Examples of silica-coated titanium oxide and silica-coated zinc oxide and Examples of cosmetic composition (formulation and production process). However, the present invention is by no means limited to these description.

The term "Silica-coated titanium oxide or silica-coated zinc oxide" in Formulation of Examples represents silica-coated titanium oxide alone, silica-coated zinc oxide alone and both silica-coated titanium oxide and silica-coated zinc oxide at the ratio of 1:4 to 2:3.

PRODUCTION EXAMPLE 1

Production of Silica-Coated Titanium Oxide

In a 5 L-volume reaction vessel, 400 mL of deionized water, 1,400 mL of ethanol (produced by Junsei Kagaku K.K.) and 75 mL of a 25 mass % aqueous ammonia (produced by Taisei Kako) were mixed and thereinto, 105 g of titanium oxide (High-Purity Titanium Oxide F-1, produced by Showa Titanium K.K.; primary particle size: 90 nm) was dispersed to prepare Suspension 1. Separately, 193 mL of tetraethoxysilane (produced by Nakarai Tesc), 36 mL of water and 144 mL of ethanol were mixed to prepare Solution 1.

To Suspension 1 under stirring with a magnetic stirrer, Solution 1 was added at a constant rate over 6 hours. The resulting solution was ripened for 12 hours. The film formation and ripening were performed at 25° C. Thereafter, the solid contents were separated by centrifugal filtration, vacuum dried at 50° C. for 12 hours and then hot air dried at 80° C. for 12 hours to obtain silica-coated titanium oxide.

PRODUCTION EXAMPLE 2

Production of Silica-Coated Titanium Oxide

Silica-coated titanium oxide was obtained in the same manner as in Production Example 1 except for using titanium oxide having a different primary particle size (High-Purity Titanium Oxide F-4 produced by Showa Titanium K.K.; primary particle size: 30 nm) in place of the titanium oxide of Production Example 1.

PRODUCTION EXAMPLE 3

Production of Silica-Coated Titanium Oxide

In a 5 L-volume reaction vessel, 420 mL of deionized water, 1,930 mL of ethanol (produced by Junsei Kagaku K.K.) and 75 mL of a 25 mass % aqueous ammonia (produced by Taisei Kako) were mixed and thereinto, 105 g of titanium oxide (High-Purity Titanium Oxide F-4, produced by Showa Titanium K.K.; primary particle size: 30 nm) was dispersed to prepare Suspension 2. Separately, 44 mL of tetraethoxysilane (produced by Nakarai Tesc) and 135 mL of ethanol were mixed to prepare Solution 2.

To Suspension 2 under stirring with a magnetic stirrer, Solution 2 was added at a constant rate over 6 hours. The resulting solution was ripened for 12 hours. The film formation and ripening were performed at 25° C. Thereafter, the solid-liquid separation and drying were performed in the same manner as in Production Example 1 and the obtained product was ground in a jet mill to obtain silica-coated titanium oxide.

PRODUCTION EXAMPLE 4

Production of Silica-Coated Zinc Oxide

In a 50 L-volume reaction vessel, 18.25 L of deionized water, 22.8 L of ethanol (produced by Junsei Kagaku K.K.) and 124 mL of a 25 mass % aqueous ammonia (produced by Taisei Kako) were mixed and thereinto, 1.74 Kg of zinc oxide (High-Purity Zinc Oxide UFZ-40, produced by Showa Titanium K.K.; primary particle size: 27 nm) was dispersed to prepare Suspension 3. Separately, 1.62 L of tetraethoxysilane (produced by GE Toshiba Silicone) and 1.26 L of ethanol were mixed to prepare Solution 3.

To Suspension 3 under stirring, Solution 3 was added at a constant rate over 9 hours. The resulting solution was ripened for 12 hours. The film formation and ripening were performed at 45° C. Thereafter, the solid-liquid separation and drying were performed in the same manner as in Production Example 1 and the obtained product was ground in a jet mill to obtain silica-coated zinc oxide.

The silica-coated titanium oxide or silica-coated zinc oxide obtained in Production Examples 1 to 4 were determined on the transmission infrared absorption spectrum by the KBr method. As a result, with any metal oxide powder, an absorption originated from the Si-O-Si stretching vibration was observed at from 1,000 to 1,200 $cm^{-1}$, and an absorption originated from the C-H stretching vibration was not observed at from 2,800 to 3,000 $cm^{-1}$, whereby the formed film was identified as silica.

Furthermore, the primary particle size, the thickness of silica film, the ratio I of absorption peak intensities on the infrared absorption spectrum, the refractive index of silica film, and the photocatalytic activity by tetralin auto-oxidation method were measured. The obtained physical properties of silica-coated titanium oxide and silica-coated zinc oxide are shown together in Table 1 below.

TABLE 1

| | Primary Particle Size, nm | Film Thickness, nm | I Value | Refractive Index | Photo-catalytic Activity, Pa/min |
|---|---|---|---|---|---|
| Production Example 1 | 90 | 10 | 0.5 | 1.445 | 3.8 |
| Production Example 2 | 30 | 4 | 0.5 | 1.445 | 4.9 |
| Production Example 3 | 30 | 1 | 0.4 | 1.440 | 4.9 |
| Production Example 4 | 27 | 3 | 0.45 | 1.443 | 3.9 |

Measurement of Light Transmittance(Cosmol Method):

The silica-coated titanium oxide of Production Examples 2 and 3 and two kinds of conventional surface-treated titanium oxide (MT500SA produced by Teica Corp. and TTO-S1 produced by Ishihara Sangyo Kaisha, Ltd.) were used as test substances and measured on the light transmittance by the Cosmol method. More specifically, each test sample was dispersed in polyglyceryl triisostearate (Cosmol 43) to prepare a slurry having a concentration of 1%, the slurry was placed in a 0.1 mm-thick quartz cell, and the light transmittance was measured by a spectrophotometer (UV-160, manufactured by SHIMADZU). The results are shown together in FIG. 1.

The silica-coated titanium oxide for use in the present invention has high light-shielding ability in the ultraviolet region and high transmittance in the visible region. Measurement of Dye Discoloration Rate(Sunset Yellow Method):

The silica-coated titanium oxide obtained in Production Examples 1 to 3, two kinds of uncoated titanium oxide corresponding to each of the products, two kinds of conventional surface-treated titanium oxide (MT500SA produced by Teica Corp. and TTO-S1 produced by Ishihara Sangyo Kaisha, Ltd.), the silica-coated zinc oxide obtained in Production Example 4 and uncoated zinc oxide were used as test substances and measured on the dye discoloration rate by the Sunset Yellow method.

More specifically, Sunset Yellow FCF (produced by Wako Pure Chemical Industries, Ltd.) as a dye for cosmetic materials was dissolved in a 98 mass % glycerin to have a dye concentration of 0.02 mass %. Each test substance was dispersed therein to have a concentration of 0.067 mass % and the resulting dispersion solution was irradiated with ultraviolet rays (ultraviolet intensity: 1.65 $mW/cm^2$). The absorbance at 490 nm which is a maximum absorption wavelength of Sunset Yellow FCF was measured to a light pass length of 1 mm by a spectrophotometer (UV-160, manufactured by SHIMADZU) with the passage of time and the difference ($\Delta ABS_{490}$/hr) between the absorbance decrease rate here and the absorbance decrease rate in a null test (no addition of titanium oxide or zinc oxide) was calculated. The results in comparison of the dye discoloration rate are shown in Table 2.

TABLE 2

| | Dye discoloration Rate ($\Delta ABS_{490}$/hr) |
|---|---|
| Production Example 1 | 0.05 |
| Production Example 2 | 0.02 |
| Production Example 3 | 0.10 |
| Production Example 4 | 0.00 |

TABLE 2-continued

| | Dye discoloration Rate ($\Delta ABS_{490}$/hr) |
|---|---|
| Conventional Surface-Treated Titanium Oxide (MT500SA) | 0.12 |
| Conventional Surface-Treated Titanium Oxide (TTO-S1) | 4.19 |
| Uncoated Titanium Oxide (starting material of Production Example 1) | 14.30 |
| Uncoated Titanium Oxide (starting material of Production Example 2) | 22.88 |
| Uncoated Zinc Oxide (starting material of Production Example 4) | 8.86 |

Any test substance of silica-coated titanium oxide or silica-coated zinc oxide for use in the present invention had a dye discoloration rate of 0.1 ($\Delta ABS_{490}$/hr) or less, revealing that the decomposition of dye was suppressed low as compared with uncoated product and conventional surface-treated product.

Measurement of Decomposition Rate of Organic Ultraviolet Absorber(Parsol Method):

The silica-coated titanium oxide obtained in Production Examples 1 to 3, two kinds of uncoated titanium oxide corresponding to each of the products, two kinds of conventional surface-treated titanium oxide (MT500SA produced by Teica Corp. and TTO-S1 produced by Ishihara Sangyo Kaisha, Ltd.), the silica-coated zinc oxide obtained in Production Example 4 and uncoated zinc oxide were used as test substances and measured on the organic ultraviolet absorber decomposition rate by the Parsol method. More specifically, each test substance was dispersed in a polyethylene glycol 300 solution of 4-tert-butyl-4'-methoxydibenzoylmethane (Parsol 1789) (0.045% by mass as a Parsol 1789 concentration) to form a 1 wt % slurry. Then, 1.2 g of the slurry was charged in a glass container, ultraviolet rays (1.65 mW/cm$^2$) were irradiated for 10 hours, 1 g was sampled and thereto, 2 mL of isopropyl alcohol, 2 mL of hexane and 3 mL of distilled water were sequentially added. The mixture was stirred, Parsol 1789 was extracted in the hexane phase, and the absorbance (340 nm) of the hexane phase was measured to a light pass length of 1 mm by a spectrophotometer (UV-160, manufactured by SHIMADZU). The difference ($\Delta ABS_{340}$/hr) between the absorbance decrease rate at 340 nm and the absorbance decrease rate in a null test (no addition of titanium oxide or zinc oxide) was calculated. The results in comparison of the organic ultraviolet absorber (Parsol 1789) decomposition rate are shown in Table 3.

TABLE 3

| | Decomposition Rate ($\Delta ABS_{340}$/hr) |
|---|---|
| Production Example 1 | 0.001 |
| Production Example 2 | 0.001 |
| Production Example 3 | 0.017 |
| Production Example 4 | 0.002 |
| Conventional Surface-Treated Titanium Oxide (MT500SA) | 0.024 |
| Conventional Surface-Treated Titanium Oxide (TTO-S1) | 0.044 |
| Uncoated Titanium Oxide (starting material of Production Example 1) | 0.120 |
| Uncoated Titanium Oxide (starting material of Production Example 2) | 0.175 |

TABLE 3-continued

| | Decomposition Rate ($\Delta ABS_{340}$/hr) |
|---|---|
| Uncoated Zinc Oxide (starting material of Production Example 4) | 0.066 |

In any test substance of silica-coated titanium oxide or silica-coated zinc oxide for use in the present invention, the decomposition rate was 0.02 ($\Delta ABS_{340}$/hr) or less, revealing that the decomposition property of ultraviolet absorber was extremely low as compared with uncoated product and conventional surface-treated product.

Measurement of Amount of Hydroxy Radical Generated:

An antioxidant mixture (50% by mass of magnesium L-ascorbic acid-2-phosphate and 50% by mass of sodium L-ascorbic acid-2-phosphate) was prepared. Silica-coated titanium oxide of Production Example 1 mixed with the antioxidant mixture at a mass ratio of 1:1, silica-coated titanium oxide alone of Production Example 1 and uncoated titanium oxide alone each was formed into a water suspension to have the same titanium oxide concentration (0.5% by mass) and measured on the amount of hydroxy radical generated under light irradiation by the electron spin resonance method using DMPO as a radical trapping agent. As a result, the amount of hydroxy radical generated was lowest when the silica-coated titanium oxide was mixed with antioxidant, next low in the case of silica-coated titanium oxide alone and highest in the case of uncoated titanium oxide.

Measurement of Powder Kinetic Friction Coefficient(glass plate method):

The silica-coated titanium oxide obtained in Production Examples 1 to 3, two kinds of uncoated titanium oxide corresponding to each of the products, two kinds of conventional surface-treated titanium oxide (MT500SA produced by Teica Corp. and TTO-S1 produced by Ishihara Sangyo Kaisha, Ltd.), the silica-coated zinc oxide obtained in Production Example 4 and uncoated zinc oxide were used as test substances and measured on the powder kinetic friction coefficient by the glass plate method. More specifically, each test substance was dispersed on a 100×200 mm glass plate to an amount of 10 mg/cm$^2$. This glass plate was placed on the test table of a surface property measuring apparatus (HEIDON) and the coefficient of kinetic friction was determined under conditions such that the load was 22.2 g/cm$^2$, the moving speed was 200 mm/min and the moving distance was 20 mm. The results in comparison of the powder kinetic friction coefficient are shown in Table 4.

TABLE 4

| | Coefficient of Powder Kinetic Friction |
|---|---|
| Production Example 1 | 0.441 |
| Production Example 2 | 0.447 |
| Production Example 3 | 0.510 |
| Production Example 4 | 0.490 |
| Conventional Surface-Treated Titanium Oxide (MT500SA) | 0.554 |
| Conventional Surface-Treated Titanium Oxide (TTO-S1) | 0.685 |
| Uncoated Titanium Oxide (starting material of Production Example 1) | 0.584 |
| Uncoated Titanium Oxide (starting material of Production Example 2) | 0.641 |

TABLE 4-continued

| | Coefficient of Powder Kinetic Friction |
|---|---|
| Uncoated Zinc Oxide (starting material of Production Example 4) | 0.640 |

In any test substance of silica-coated titanium oxide or silica-coated zinc oxide for use in the present invention, the coefficient of kinetic friction is 0.550 or less, whereas the value exceeded 0.550 in the case of uncoated product and conventional surface-treated product.

Test of Change in Viscosity of Carboxyvinyl Polymer Solution:

In order to examine the aptitude for use of the silica-coated titanium oxide or silica-coated zinc oxide in the cosmetic composition of the present invention, titanium oxide or zinc oxide was dispersed in an aqueous solution of carboxyvinyl polymer and the viscosity of slurry obtained was measured. More specifically, 0.133 wt % of CARBOPOL C940 produced by BFGoodrich as a carboxyvinyl polymer was dissolved in distilled water, the pH was adjusted to 6.5 by adding 10% potassium hydroxide, 10 wt % of titanium oxide or zinc oxide was charged thereinto and dispersed under stirring by a homomixer at 5,000 rpm for 5 minutes. The titanium oxide or zinc oxide tested were the silica-coated titanium oxide obtained in Production Examples 1 to 3, two kinds of uncoated titanium oxide corresponding to each of the products, two kinds of conventional surface-treated titanium oxide (MT500SA produced by Teica Corp. and TTO-S1 produced by Ishihara Sangyo Kaisha, Ltd.), the silica-coated zinc oxide obtained in Production Example 4 and uncoated zinc oxide. The viscosity of each obtained slurry was measured at 25° C. by a B-type viscometer with the passage of time. During the measurement, the test substances were stored at 25° C. in a dark place. The results of change in the viscosity of titanium oxide-dispersed slurry are shown in Table 5.

TABLE 5

| | Slurry Viscosity (cps) | | |
|---|---|---|---|
| | Initial viscosity | After 100 Hours | After 170 Hours |
| No addition of Titanium Oxide or Zinc Oxide | 19800 | 19300 | 18500 |
| Production Example 1 | 28300 | 22000 | 20000 |
| Production Example 2 | 26500 | 24300 | 19500 |
| Production Example 3 | 18500 | 14250 | 13500 |
| Production Example 4 | 18500 | 12000 | 10800 |
| Conventional Surface-Treated Titanium Oxide (MT500SA) | 20000 | 3500 | ≦500 |
| Conventional Surface-Treated Titanium Oxide (TTO-S1) | 8500 | 1600 | ≦500 |
| Uncoated Titanium Oxide (starting material of Production Example 1) | 8750 | 8000 | 7500 |
| Uncoated Titanium Oxide (starting material of Production Example 2) | 3600 | 3500 | 3400 |
| Uncoated Zinc Oxide (starting material of Production Example 4) | 2100 | ≦500 | ≦500 |

The silica-coated titanium oxide or silica-coated zinc oxide for use in the present invention has no reactivity with the carboxyvinyl polymer and the high viscosity of the polymer aqueous solution was maintained after the passing of time. On the other hand, the viscosity of uncoated product and conventional surface-treated product greatly decreased from the initial viscosity.

In order to examine the effect of titanium oxide on the ultraviolet deterioration of carboxyvinyl polymer, the slurry of conventional surface-treated product was further irradiated with ultraviolet rays (1.65 mW/cm$^2$, 1 hr) and the viscosity was measured in the same manner. The results of change in the viscosity of titanium oxide-dispersed slurry due to the irradiation of ultraviolet rays are shown in Table 6.

TABLE 6

| | Slurry Viscosity (cps) | |
|---|---|---|
| | Initial viscosity | After Irradiation of Ultraviolet Rays |
| No addition of Titanium Oxide or Zinc Oxide | 19300 | 13000 |
| Production Example 1 | 28300 | 27000 |
| Production Example 2 | 26500 | 25000 |
| Production Example 3 | 18500 | 16200 |
| Conventional Surface-Treated Titanium Oxide (MT500SA) | 20000 | 12700 |
| Conventional Surface-Treated Titanium Oxide (TTO-S1) | 8500 | 5000 |
| Uncoated Titanium Oxide (starting material of Production Example 1) | 8750 | 5000 |
| Uncoated Titanium Oxide (starting material of Production Example 2) | 3600 | 2000 |

The silica-coated titanium oxide for use in the present invention has high ultraviolet shielding ability and at the same time, the photocatalytic effect thereof is sufficiently suppressed, so that the ultraviolet deterioration of carboxyvinyl polymer can be prevented and the high viscosity of polymer aqueous solution can be maintained after the irradiation of ultraviolet rays. On the other hand, in the case of uncoated titanium oxide and conventional surface-treated titanium oxide, the photocatalytic activity is not sufficiently suppressed and the gel structure of carboxyvinyl polymer is denatured, as a result, the viscosity is greatly decreased by the irradiation of ultraviolet rays.

Measurement of Eluting Metal Ion of Titanium Oxide or Zinc Oxide:

The carboxyvinyl polymer deteriorates in the preparation form stability due to the effect of metal ion, because the hydration degree of polymer is reduced by the reaction between metal ion and carboxyl group and therefore, the viscosity decreases. In the case of using titanium oxide or zinc oxide with a carboxyvinyl polymer in combination, the viscosity decreases along the elution of ion and the preparation form stability is deteriorated. Among metal ions, polyvalent ion such as calcium and magnesium have a large effect on the reduction of viscosity. In the case of zinc oxide, zinc ion eluted along the dissolution of zinc oxide is also known to have a serious effect on the reduction of viscosity.

Accordingly, in order to examine the aptitude for use of the silica-coated titanium oxide or silica-coated zinc oxide in the cosmetic composition of the present invention, the contents of calcium ion and magnesium ion as eluting metal ion were measured. More specifically, silica-coated titanium oxide or silica-coated zinc oxide was added to an eluent (5 mM tartaric acid, 1 mM dipicolinic acid) to have an appropriate concentration and dispersed at 25° C. with ultrasonic wave of 24 KHz for 10 minutes. The ion amount of its supernatant was measured by ion chromatography.

The ion chromatography was performed under the conditions such that the column was Shodex (a registered trademark) IC Pack YK-421 (produced by Showa Denko K.K.), the column temperature was 40° C., the eluent was the same as the above-described eluent, the flow rate of eluent was 1 ml/min and the electrical conductivity was detected. The titanium oxide or zinc oxide tested were the silica-coated titanium oxide obtained in Production Examples 1 to 3, two kinds of conventional surface-treated titanium oxide (MT500SA produced by Teica Corp. and TTO-S1 produced by Ishihara Sangyo Kaisha, Ltd.) and the silica-coated zinc oxide obtained in Production Example 4. The results of comparison in the eluting metal ion of titanium oxide and zinc oxide are shown in Table 7.

TABLE 7

|  | Eluting Metal Ion (ppm) | |
| --- | --- | --- |
|  | $Ca^{2+}$ | $Mg^{2+}$ |
| Production Example 1 | <5 | <5 |
| Production Example 2 | <5 | <5 |
| Production Example 3 | <5 | <5 |
| Production Example 4 | <5 | <5 |
| Conventional Surface-Treated Titanium Oxide (MT500SA) | 72 | 83 |
| Conventional Surface-Treated Titanium Oxide (TTO-S1) | 16 | <5 |

The silica-coated titanium oxide or silica-coated zinc oxide of the present invention was very reduced in the eluting calcium ion or magnesium ion. This suggests that the hydration degree of carboxy polymer does not decrease and the viscosity can be maintained. On the other hand, conventional surface-treated titanium oxide contained a large amount of eluting calcium ion or magnesium ion and therefore, accompanying the elution of ion, the hydration degree of carboxyvinyl polymer decreased to cause reduction in the viscosity.

Furthermore, in order to examine the aptitude for use of the silica-coated zinc oxide in the cosmetic composition of the present invention, the amount of zinc ion eluted was measured. More specifically, silica-coated zinc oxide and uncoated zinc oxide each was dispersed in solutions having various pH values to a concentration of 5% by mass. After stirring at 25° C. for 3 hours, the solution was subjected to centrifugal precipitation and the amount of zinc ion in the supernatant was measured by ICP. The results are shown in Table 8.

TABLE 8

|  | Eluted Zinc Ion (ppm) | | |
| --- | --- | --- | --- |
|  | Pure Water pH 6.4 | 1% $NH_3$ Solution pH 11.4 | 0.01% Nitric Acid Solution pH 2.5 |
| Production Example 4 | <0.5 | 20 | 9.0 |
| Uncoated Zinc Oxide | 8.0 | 480 | 91 |

EXAMPLES 1 to 4

O/W Sunscreen Milky Lotion

| Formulation of O/W Sunscreen Milky Lotion | |
| --- | --- |
| Aqueous Phase | |
| Purified water | 70.8 mass % |
| Silica-coated titanium oxide or silica-coated zinc oxide | 7.0 mass % |
| 1,3-Butylene glycol | 2.0 mass % |
| CARBOPOL C980 | 0.2 mass % |
| Triethanolamine | 1.0 mass % |
| Oil Phase | |
| Octyl p-methoxycinnamate | 3.0 mass % |
| Isopropyl myristate | 2.0 mass % |
| Oleyl oleate | 4.0 mass % |
| Petrolatum | 2.0 mass % |
| Stearyl alcohol | 1.0 mass % |
| Stearic acid | 2.0 mass % |
| Glyceryl monostearate | 2.0 mass % |
| Vitamin E acetate | optimum |
| Antiseptic | optimum |
| Perfume | optimum |

Production Process:

The oil phase part and the aqueous phase part each was dissolved under heat at 70° C. For thoroughly dispersing titanium oxide or zinc oxide in the aqueous phase part, titanium oxide or zinc oxide was added after the dissolution of ingredients blended in the aqueous phase and uniformly dispersed by a homomixer and the dispersion was kept at 70° C. The oil phase was added to the aqueous phase and the mixture was emulsified using a homomixer. After the emulsification, the emulsion was cooled to 35° C. while stirring to obtain a sunscreen milky lotion having the following formulation. The silica-coated titanium oxide or silica-coated zinc oxide used was four kinds of silica-coated titanium oxide or silica-coated zinc oxide obtained in Production Examples 1 to 4. The sunscreen milky lotions obtained above were evaluated on the preparation form stability during storage (at 25° C.), as a result, creaming was not observed within 7 days and stable emulsion stage was maintained. The use property was good.

EXAMPLES 5 to 8

O/W Sunscreen Cream

| Formulation of O/W Sunscreen Cream | |
| --- | --- |
| Aqueous Phase | |
| Purified water | 54.8 mass % |
| Silica-coated titanium oxide or silica-coated zinc oxide | 5.0 mass % |
| 1,3-Butylene glycol | 7.0 mass % |
| CARBOPOL C980 | 0.2 mass % |
| Triethanolamine | 1.0 mass % |
| Oil Phase | |
| Octyl p-methoxycinnamate | 5.0 mass % |
| 4-tert-Butyl-4'-methoxybenzoylmethane | 1.0 mass % |
| Squalane | 11.0 mass % |
| Petrolatum | 5.0 mass % |
| Stearyl alcohol | 3.0 mass % |
| Stearic acid | 3.0 mass % |
| Glyceryl monostearate | 3.0 mass % |

-continued

| Formulation of O/W Sunscreen Cream | |
|---|---|
| Ethyl polyacrylate | 1.0 mass % |
| Antioxidant | optimum |
| Antiseptic | optimum |
| Perfume | optimum |

Production Process:

The oil phase part and the aqueous phase part each was dissolved under heat at 70° C. For thoroughly dispersing titanium oxide or zinc oxide in the aqueous phase part, titanium oxide or zinc oxide was added after the dissolution of ingredients blended in the aqueous phase and uniformly dispersed by a homomixer and the dispersion was kept at 70° C. The oil phase was added to the aqueous phase and the mixture was emulsified using a homomixer. After the emulsification, the emulsion was cooled to 35° C. while stirring to obtain a sunscreen cream having the following formulation. The silica-coated titanium oxide or silica-coated zinc oxide used was four kinds of silica-coated titanium oxide or silica-coated zinc oxide obtained in Production Examples 1 to 4. The sunscreen Milky Lotion obtained above were evaluated on the preparation form stability during storage (at 25° C.), as a result, creaming was not observed within 7 days and stable emulsion stage was maintained. The use property was good.

EXAMPLES 9 to 12

Skin Lotion

| Formulation of Skin Lotion | |
|---|---|
| Silica-coated titanium oxide or silica-coated zinc oxide | 3.0 mass % |
| Ethyl alcohol | 10.0 mass % |
| Sorbitol | 4.0 mass % |
| Dipropylene glycol | 6.0 mass % |
| Polyethylene glycol 1500 | 5.0 mass % |
| Polyoxyethylene (20) oleyl alcohol ether | 0.5 mass % |
| CARBOPOL C980 | 0.2 mass % |
| Vitamin C derivative | 3.0 mass % |
| Purified water | 42.8 mass % |
| Buffer | optimum |
| Antiseptic | optimum |
| Perfume | optimum |

Production Process:

CARBOPOL was mixed with a part of purified water and stirred to prepare a viscous solution. To the residue of purified water, a humidity retainer, a buffer solution and the like were added and dissolved at room temperature and thereafter, titanium oxide or zinc oxide were added and dispersed by a homomixer. To this solution, the viscous solution prepared above was added and a uniform aqueous solution was obtained by a homomixer. An antiseptic, a surfactant and a perfume were added to ethanol to prepare an alcohol solution and this solution was added to the aqueous solution prepared above and mixed to perform the solubilization. The silica-coated titanium oxide or silica-coated zinc oxide used were four kinds of silica-coated titanium oxide or silica-coated zinc oxide obtained in Production Examples 1 to 4. The skin lotions obtained above were evaluated on the preparation form stability during storage (at 25° C.), as a result, reduction of viscosity was not observed within 7 days and the use property was good.

EXAMPLES 13 to 16

Whitening Essence

| Formulation of Whitening Essence | |
|---|---|
| Silica-coated titanium oxide or silica-coated zinc oxide | 3.0 mass % |
| Ethyl alcohol | 10.0 mass % |
| Dipropylene glycol | 5.0 mass % |
| Polyethylene glycol 400 | 5.0 mass % |
| Polyoxyethylene sorbitan monostearate | 0.5 mass % |
| Sorbitan monooleate | 0.5 mass % |
| CARBOPOL C980 | 0.2 mass % |
| Potassium hydroxide | 0.15 mass % |
| Placenta extract | 0.2 mass % |
| Oleyl alcohol | 0.5 mass % |
| Vitamin E acetate | 0.2 mass % |
| Purified water | 73.85 mass % |
| Antiseptic | optimum |
| Perfume | optimum |

Production Process:

CARBOPOL was mixed with a part of purified water and stirred to prepare a viscous solution. To the residue of purified water, a humidity retainer and the like were added and dissolved at room temperature and thereafter, titanium oxide or zinc oxide were added and dispersed by a homomixer. To this solution, the viscous solution prepared above was added and a uniform aqueous solution was obtained by a homomixer. A surfactant, an emollient, a vitamin E acetate, a perfume and an antiseptic were sequentially added to ethanol and the resulting solution was added to the aqueous solution prepared above and formed into a microemulsion. Finally, potassium hydroxide was dissolved in a part of purified water and this solution was added and stirred. The silica-coated titanium oxide or silica-coated zinc oxide used were four kinds of silica-coated titanium oxide or silica-coated zinc oxide obtained in Production Examples 1 to 4. The whitening essences obtained above were evaluated on the preparation form stability during storage (at 25° C.), as a result, reduction of viscosity was not observed within 7 days and the use property was good.

EXAMPLES 17 to 20

Moisture Jell

| Formulation of Moisture Jell | |
|---|---|
| Silica-coated titanium oxide or silica-coated zinc oxide | 3.0 mass % |
| Dipropylene glycol | 7.0 mass % |
| Polyethylene glycol 1500 | 8.0 mass % |
| Polyoxyethylene (15) oleyl alcohol ether | 1.0 mass % |
| CARBOPOL C980 | 0.2 mass % |
| Methyl cellulose | 0.2 mass % |
| Potassium hydroxide | 0.1 mass % |
| Purified water | 80.5 mass % |
| Antiseptic | optimum |
| Perfume | optimum |
| Chelating agent | optimum |

Production Process:

CARBOPOL was uniformly dissolved in a part of purified water and thereto, polyethylene glycol and a chelating agent were added. Furthermore, titanium oxide or zinc oxide was added and dispersed by a homomixer. A surfactant was added to dipropylene glycol and dissolved under heat at 50 to 55° C. and thereto, an antiseptic and a perfume were added. This solution was added to the previously prepared aqueous phase and stirred. The silica-coated titanium oxide or silica-coated zinc oxide used were four kinds of silica-coated titanium oxide or silica-coated zinc oxide obtained in Production Examples 1 to 4. The moisture jells obtained above were evaluated on the preparation form stability during storage (at 25° C.), as a result, reduction of viscosity was not observed within 7 days and the use property was good.

COMPARATIVE EXAMPLES 1 to 4

O/W Sunscreen milky lotions were prepared using two kinds of corresponding uncoated titanium oxide and two kinds of conventional surface-treated titanium oxide (MT500SA produced by Teica Corp. and TTO-S1 produced by Ishihara Sangyo Kaisha, Ltd.) in place of the silica-coated titanium oxide in the formulations of Examples 1 to 4. The thus -prepared O/W sunscreen milky lotions of Comparative Examples 1 to 4 were evaluated on the preparation form stability during storing (at 25° C.), as a result, creaming was caused after 7 days in any product and the use property was bad.

COMPARATIVE EXAMPLES 5 to 8

O/W Sunscreen creams were prepared using two kinds of corresponding uncoated titanium oxide and two kinds of conventional surface-treated titanium oxide (MT500SA produced by Teica Corp. and TTO-S1 produced by Ishihara Sangyo Kaisha, Ltd.) in place of the silica-coated titanium oxide in the formulations of Examples 5 to 8. The thus-prepared O/W sunscreen creams of Comparative Examples 5 to 8 were evaluated on the preparation form stability during storing (at 25° C.), as a result, creaming was caused after 7 days in any product and the use property was bad.

COMPARATIVE EXAMPLES 9 to 12

Skin lotions were prepared using two kinds of corresponding uncoated titanium oxide and two kinds of conventional surface-treated titanium oxide (MT500SA produced by Teica Corp. and TTO-S1 produced by Ishihara Sangyo Kaisha, Ltd.) in place of the silica-coated titanium oxide in the formulations of Examples 9 to 12. The thus-prepared skin lotions of Comparative Examples 9 to 12 were evaluated on the preparation form stability during storing (at 25° C.), as a result, the viscosity was decreased after 7 days in any product and the use property was bad.

COMPARATIVE EXAMPLES 13 to 16

Whitening essences were prepared using two kinds of corresponding uncoated titanium oxide and two kinds of conventional surface-treated titanium oxide (MT500SA produced by Teica Corp. and TTO-S1 produced by Ishihara Sangyo Kaisha, Ltd.) in place of the silica-coated titanium oxide in the formulations of Examples 13 to 16. The thus-prepared whitening essences of Comparative Examples 13 to 16 were evaluated on the preparation form stability during storing (at 25° C.), as a result, the viscosity was decreased after 7 days in any product and the use property was bad.

COMPARATIVE EXAMPLES 17 to 20

Moisture jells were prepared using two kinds of corresponding uncoated titanium oxide and two kinds of conventional surface-treated titanium oxide (MT500SA produced by Teica Corp. and TTO-S1 produced by Ishihara Sangyo Kaisha, Ltd.) in place of the silica-coated titanium oxide in the formulations of Examples 17 to 20. The thus-prepared moisture jells of Comparative Examples 17 to 20 were evaluated on the preparation form stability during storing (at 25° C.), as a result, the viscosity was decreased after 7 days in any product and the use property was bad.

INDUSTRIAL APPLICABILITY

The cosmetic composition of the present invention, comprising titanium oxide coated with one or both of silica and alumina or zinc oxide coated with one or both of silica and alumina, and a thickening polymer having a carboxyl group in the side chain, can maintain emulsion stability by thickening of carboxyvinyl polymer for a long period of time and can be widely and suitably used for ultraviolet shielding cosmetic materials or the like having preparation form stability.

What is claimed is:

1. A cosmetic composition comprising titanium oxide coated with a dense silica film having a film thickness of 0.1 to 100 nm and a refractive index of 1.435 or more or zinc oxide coated with a dense silica film having a film thickness of 0.1 to 100 nm and a refractive index of 1.435 or more, and a thickening polymer having a carboxyl group in the side chain.

2. The cosmetic composition as claimed in claim 1, wherein the thickening polymer having a carboxyl group in the side chain is at least one polymer selected from a group consisting of carboxyvinyl polymer, carboxymethyl cellulose, carboxymethyl starch, poly(sodium acrylate), alginic acid propylene glycol ester and alginic acid salt.

3. The cosmetic composition as claimed in claim 2, wherein the thickening polymer having a carboxyl group in the side chain is carboxyvinyl polymer.

4. The cosmetic composition as claimed in claim 3, wherein when titanium oxide coated with silica or zinc oxide coated with silica is dispersed by 10% by mass in an aqueous solution containing 0.133% by mass of a carboxyvinyl polymer, the viscosity after passing of 100 hours is 60% or more of the initial viscosity.

5. The cosmetic composition as claimed in claim 4, wherein when titanium oxide coated with silica is dispersed by 10% by mass in an aqueous solution containing 0.133% by mass of a carboxyvinyl polymer, the viscosity after passing of 100 hours is 70% or more of the initial viscosity.

6. The cosmetic composition as claimed in claim 4, wherein when zinc oxide coated with silica is dispersed by 10% by mass in an aqueous solution containing 0.133% by mass of a carboxyvinyl polymer, the viscosity after passing of 100 hours is 60% or more of the initial viscosity.

7. The cosmetic composition as claimed in claim 1, wherein photocatalytic activity of the silica-coated titanium oxide or silica-coated zinc oxide determined by a tetralin auto-oxidation method is 60 Pa/min or less.

8. The cosmetic composition as claimed in claim 1, wherein the silica-coated titanium oxide or silica-coated zinc oxide has a primary particle size of 5 to 200 nm.

9. The cosmetic composition as claimed in claim 1, wherein a ratio of absorption peak intensity at 1,150 to 1,250 cm$^{-1}$ to absorption peak intensity at 1,000 to 1,100 cm$^{-1}$ on the infrared absorption spectrum ($I=I_1/I_2$, wherein $I_1$ is absorption peak intensity at 1,150 to 1,250 cm$^{-1}$ and $I_2$ is absorption peak intensity at 1,000 to 1,100 cm$^{-1}$) is 0.2 or more.

10. The cosmetic composition as claimed in claim 1, wherein a dye discoloration rate ($\Delta ABS_{490}$/hr) of the silica-coated titanium oxide or silica-coated zinc oxide measured by the Sunset Yellow method is 0.1 or less.

11. The cosmetic composition as claimed in claim 1, wherein an organic ultraviolet absorber decomposition rate (ΔABS340/hr) of the silica-coated titanium oxide or silica-coated zinc oxide measured by the Parsol method is 0.01 or less.

12. The cosmetic composition as claimed in claim 1, wherein silica-coated titanium oxide or silica-coated zinc oxide is blended in an amount of 0.1 to 50% by mass based on the entire amount of cosmetic composition.

13. A silica-coated titanium oxide or silica-coated zinc oxide for the cosmetic composition described in any one of claims 1 to 12, which is obtained by coating titanium oxide or zinc oxide with a silica film-forming composition containing (1) a silicic acid having neither an organic group nor a halogen, or a precursor capable of producing the silicic acid, (2) water, (3) an alkali and (4) an organic solvent.

14. The silica-coated titanium oxide or silica-coated zinc oxide as claimed in claim 13, which is obtained by contacting titanium oxide or zinc oxide with the silica film-forming composition having a water/organic solvent ratio (volume) of 0.1 to 10 and a silicic acid concentration of 0.0001 to 5 mol/liter to selectively deposit silica on the surface of titanium oxide or zinc oxide.

15. A method for producing a silica-coated titanium oxide or silica-coated zinc oxide for the cosmetic composition described in any one of claims 1 to 12, comprising coating titanium oxide or zinc oxide with a silica film-forming composition containing (1) a silicic acid having neither an organic group nor a halogen or a precursor capable of producing the silicic acid, (2) water, (3) an alkali and (4) an organic solvent.

16. The method for producing the silica-coated titanium oxide or silica-coated zinc oxide as claimed in claim 15, comprising contacting titanium oxide or zinc oxide with the silica film-forming composition having a water/organic solvent ratio (volume) of 0.1 to 10 and a silicic acid concentration of 0.0001 to 5 mol/liter to selectively deposit silica on the surface of titanium oxide or zinc oxide.

* * * * *